US00PP23378P2

(12) United States Plant Patent
Pullen et al.

(10) Patent No.: US PP23,378 P2
(45) Date of Patent: Feb. 5, 2013

(54) STRAWBERRY PLANT NAMED 'DRISSTRAWTWENTYFOUR'

(50) Latin Name: *Fragaria×ananassa*
Varietal Denomination: DrisStrawTwentyFour

(75) Inventors: Esther J. Pullen, Valrico, FL (US); Philip J. Stewart, Watsonville, CA (US); Kristie L. Gilford, Dover, FL (US); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 13/200,895

(22) Filed: Oct. 4, 2011

(51) Int. Cl.
*A01H 5/00* (2006.01)

(52) U.S. Cl. ..... Plt./209

(58) Field of Classification Search ..... Plt./209
See application file for complete search history.

*Primary Examiner* — Annette Para
(74) *Attorney, Agent, or Firm* — Jondle & Associates, P.C.

(57) ABSTRACT

A new and distinct variety of strawberry plant named 'DrisStrawTwentyFour' characterized by having very large sized, conical fruit with medium sweetness and high yield is disclosed.

3 Drawing Sheets

Genus and species: *Fragaria×ananassa.*
Variety denomination: 'DrisStrawTwentyFour'.

BACKGROUND OF THE NEW PLANT

The present invention relates to a new and distinct strawberry variety designated 'DrisStrawTwentyFour' and botanically known as *Fragaria×ananassa*. This new strawberry variety was discovered in Hillsborough County, Fla. in December 2007 and originated from a cross between the proprietary female parent '3M44' (unpatented) and the proprietary male parent '50L174' (unpatented). A single plant was selected for asexual propagation via tissue culture and vegetative cuttings in Shasta County, Calif. in 2007.

'DrisStrawTwentyFour' underwent further testing in Hillsborough County, Fla. for five years (2007-2011). The present invention has been found to retain its distinctive characteristics through successive asexual propagations via stolons and tissue culture.

Plant Breeder's Rights for this variety have not been applied for. 'DrisStrawTwentyFour' has not been made publicly available or sold more than one year prior to the filing date of this application.

SUMMARY OF THE INVENTION

The following are the most outstanding and distinguishing characteristics of this new cultivar when grown under normal horticultural practices in Hillsborough County, Fla.

1. High yield;
2. Very large, conic shaped fruit; and
3. Medium sweetness.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from four-month-old plants.

DESCRIPTION OF THE NEW VARIETY

Figure 1:
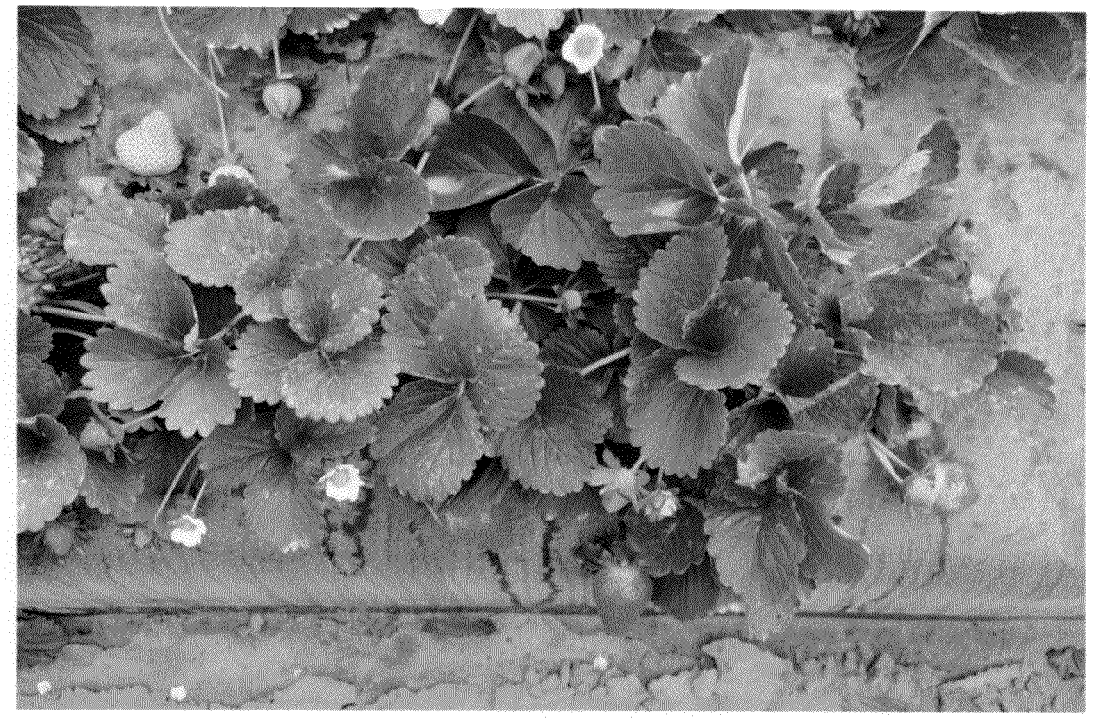
FIG. 1 shows overall plant habit including fruit at various stages of development.
Figure 2:
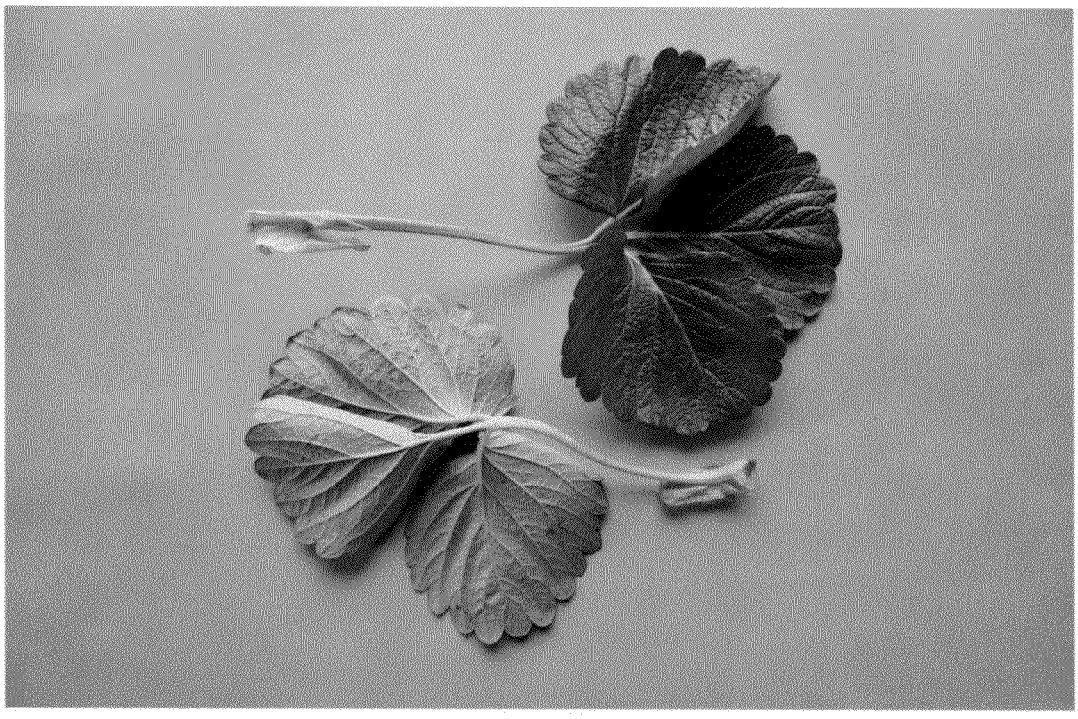
FIG. 2 shows upper and lower surfaces of the leaves of the plant with three leaflets.
Figure 3:
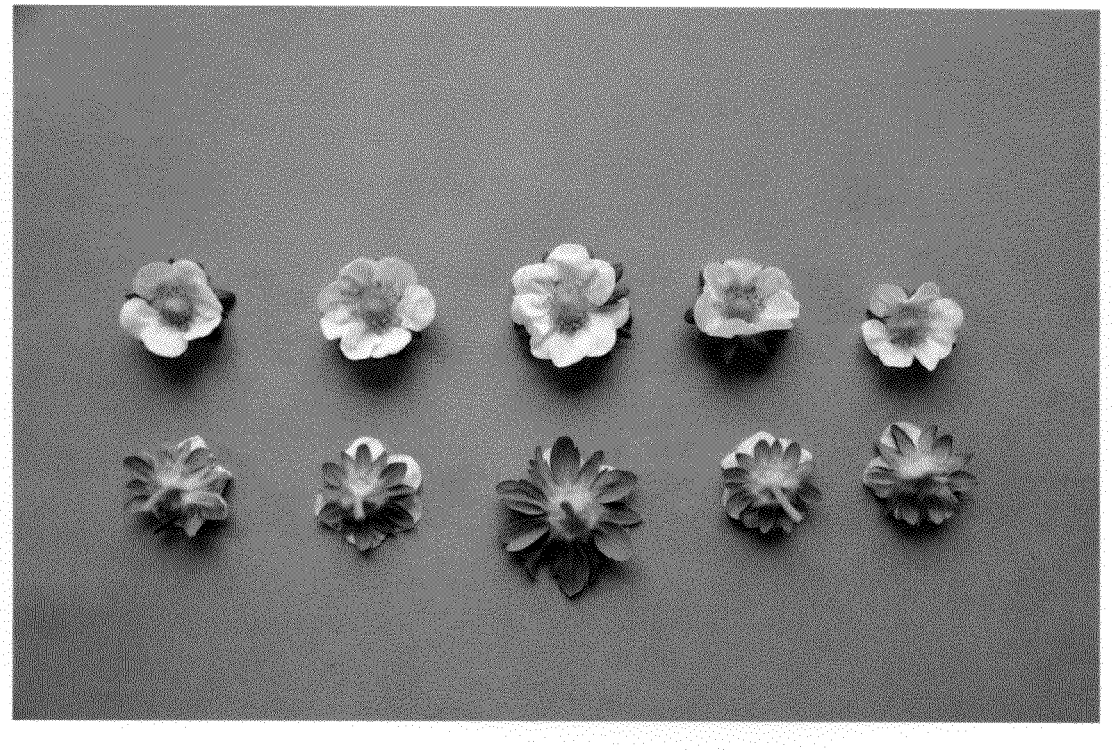
FIG. 3 shows both upper and lower surfaces of the flowers.
Figure 4:
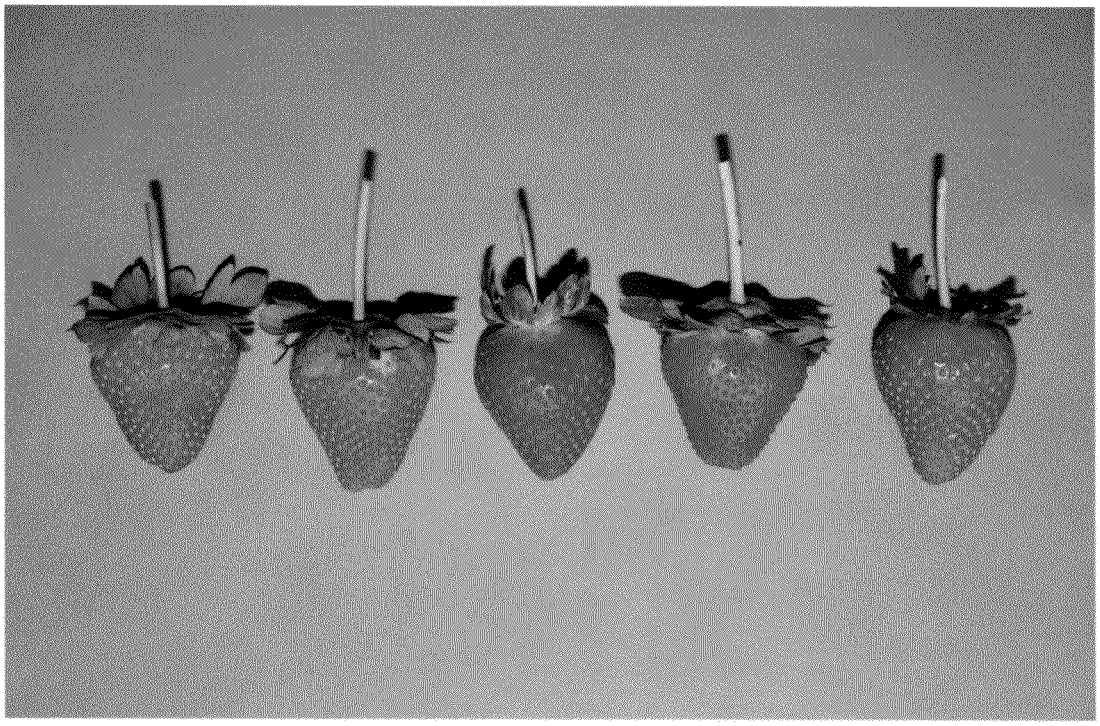
FIG. 4 shows the whole fruit.
Figure 5:
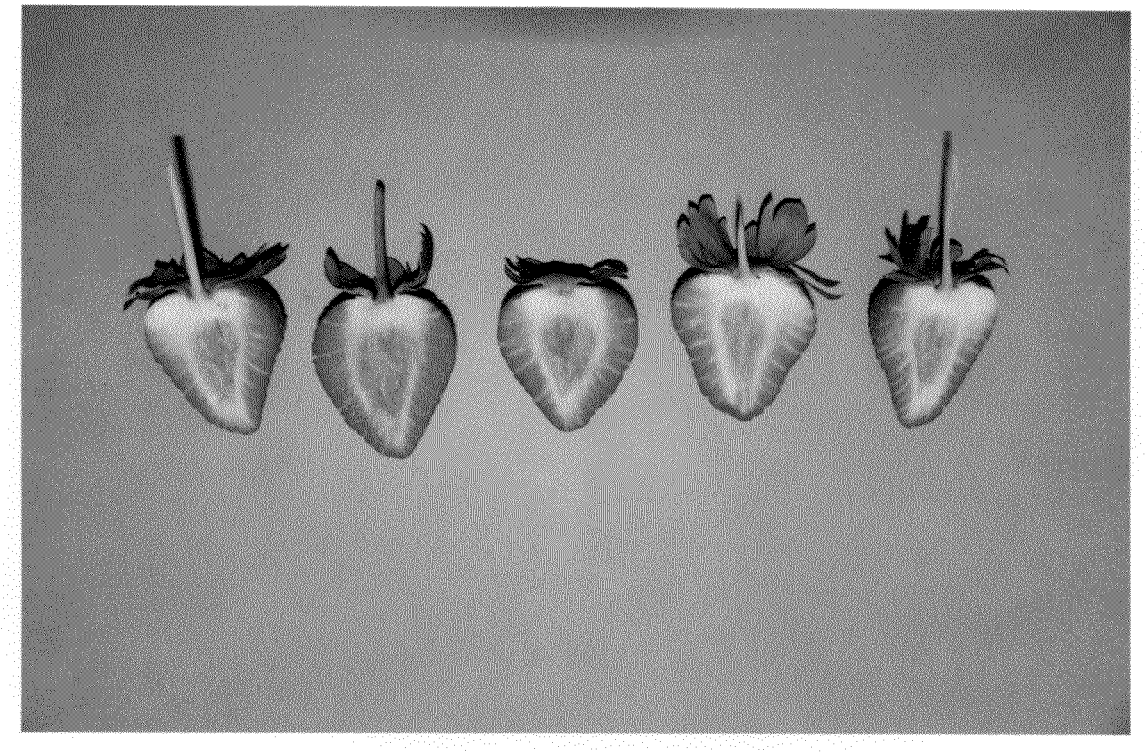
FIG. 5 shows the fruit in longitudinal cross-section.

The following detailed descriptions set forth the distinctive characteristics of 'DrisStrawTwentyFour'. The data which define these characteristics is based on observations taken in Hillsborough County, Fla. from 2007 to 2011. This description is in accordance with UPOV terminology. Color designations, color descriptions, and other phenotypical descriptions may deviate from the stated values and descriptions depending upon variation in environmental, seasonal, climatic, and cultural conditions. 'DrisStrawTwentyFour' has not been observed under all possible environmental conditions. The botanical description of 'DrisStrawTwentyFour' was taken from four-month-old plants. Color references are primarily to The R.H.S. Colour Chart of The Royal Horticultural Society of London (R.H.S.) (2001 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawTwentyFour'.

Parentage:

*Female parent.*—The proprietary variety '3M44' (unpatented).
*Male parent.*—The proprietary variety '50L174' (unpatented).

Plant:
*Height*.—19.6 cm.
*Diameter*.—42.5 cm.
*Number of crowns/plant*.—3.
*Habit*.—Flat — spreading.
*Density of individual plant*.—Open — sparse to medium.
*Vigor* (*health and hardiness of plant*).—Medium.

Terminal leaflets:
*Size*.—Medium. Length: 9.0 cm. Width: 8.3 cm. Length/width ratio: 1.1 (As long as broad).
*Number of teeth/terminal leaflet*.—21.
*Shape of teeth*.—Rounded — crenate.
*Color*.—Upper surface: RHS 173A (Dark green). Lower surface: RHS 147C (Medium yellow-green).
*Shape in cross section*.—Slightly concave.
*Blistering*.—Medium.
*Glossiness*.—Medium.
*Number of leaflets*.—Three only.
*Shape*.—Orbicular.
*Base shape*.—Slightly oblique.
*Apex descriptor*.—Rounded.
*Variegation*.—Absent.
*Margin*.—Crenate.
*Margin profile*.—Flat (level with the leaflet blade).

Petiole:
*Length*.—11.2 cm.
*Diameter*.—3.66 mm.
*Pubescence*.—Medium.
*Pose of hairs*.—Outwards-horizontal.
*Color*.—RHS N144A (Medium yellow-green).

Petiolule:
*Length*.—14.30 mm.
*Diameter*.—1.87 mm.
*Bract frequency*.—0.
*Color*.—RHS N144A (Medium yellow-green).

Stipule:
*Length*.—3.9 cm.
*Width*.—10.94 mm.
*Pubescence*.—Dense.
*Stipule anthocyanin coloration*.—Absent or very weak; RHS 182A (Dark greyed-green).

Stolon:
*Number*.—Medium.
*Average number of daughter plants per plant*.—73.
*Stolon anthocyanin*.—Strong; RHS 45A (Medium red).
*Thickness*.—Thin.
*Pubescence*.—Sparse.

Inflorescence:
*Position relative to foliage*.—Beneath.
*Number of flowers*.—Medium.
*Time of flowering* (*50% of plants at first flower*).—Very early.
*Flower size*.—Medium.
*Diameter*.—33.72 mm.
*Petals*.—Shape: Orbicular. Apex: Rounded. Base: Concavo-convex. Margin: Entire. Spacing: Overlapping. Length: 14.07 mm. Width: 14.10 mm. Length/width ratio: As long as broad; 1.0. Typical and observed petal number per flower: 7. Color (upper surface): RHS 155D (White).
*Calyx*.—Diameter.—35.10 mm. Diameter relative to corolla: Larger. Inner calyx diameter relative to outer: Same size. Insertion of calyx: Set above fruit — raised. Pose of calyx segments: All poses are present. Size of calyx in relation to fruit: Slightly larger. Adherence of calyx: Very strong.
*Sepal*.—Shape: Oval. Apex: Convex. Margin: Entire. Length: 12.50 mm. Width: 6.40 mm. Typical and observed sepal number per flower: 12 or 14.
*Receptacle color*.—RHS 145A (Medium yellow-green).
*Stamen*.—Present. Anther color: RHS 20A (Medium yellow-orange).
*Pedicel*.—Attitude of hairs: Upwards.

Fruiting truss:
*Length*.—Medium; 17.8 cm.
*Diameter at base of truss*.—3.20 mm.
*Number of berries per fruiting truss*.—1.
*Attitude at first picking*.—Prostrate.
*Color at base of truss*.—RHS 145A (Medium yellow-green).

Fruit:
*Relative fruit size*.—Very large.
*Length*.—56.95 mm.
*Width*.—45.06 mm.
*Length/width ratio*.—1.3 (Longer than broad).
*Fruit hollow length*.—34.91 mm.
*Fruit hollow width*.—15.57 mm.
*Fruit hollow length/width ratio*.—2.2.
*Fruit hollow center* (*cavity*).—Large.
*Weight* (*per individual berry*).—28.4 g.
*Predominant fruit shape*.—Conical.
*Difference in shape between primary and secondary fruits*.—Slight.
*Evenness of fruit surface*.—Even or very slightly uneven.
*Fruit skin color*.—RHS 46B (Dark red).
*Evenness of fruit color*.—Slightly uneven.
*Fruit glossiness*.—Strong.
*Achenes*.—Insertion of achenes: Above surface. Coloration (sunward side of berry): RHS 185A (Dark greyed-purple). Coloration (shaded side of berry): RHS 153D (Medium yellow-green). Number per berry: 348. Weight (weight achenes divided by total # seed): 0.0006758829. Width of band without achenes: Broad.
*Firmness of flesh*.—Firm.
*Color of flesh* (*excluding core*).—RHS 44A (Medium red) and RHS 155B (White).
*Color of core*.—RHS 39B (Medium red).
*Evenness of flesh color*.—Even.
*Distribution of flesh color*.—Only marginal.
*Sweetness*.—Medium.
*Acidity*.—Medium.
*Texture when tasted*.—Coarse.
*Type of bearing*.—Partially everbearing — partially remontant.
*Grams of fruit/plant*.—682.0 g.
*Harvest interval*.—Late November — late March.
*Harvest maturity*.—Very early.

Disease, pest, and stress resistance:
*Botrytis fruit rot*.—Susceptible.
*Powdery mildew*.—Susceptible.
*Verticillium wilt*.—Susceptible.
*Xanthomonas fragariae*.—Susceptible.
*High temperatures*.—Moderately resistant.

*High pH*.—Moderately resistant.
*Cool weather/freezes*.—Moderately resistant.

COMPARISON WITH PARENTAL AND COMMERCIAL VARIETIES

When 'DrisStrawTwentyFour' is compared to the proprietary female parent '3M44' (unpatented), 'DrisStrawTwentyFour' has earlier production and softer fruit than '3M44'.

When 'DrisStrawTwentyFour' is compared to the proprietary male parent '50L174' (unpatented), 'DrisStrawTwentyFour' has much higher yields than '50L174'.

When 'DrisStrawTwentyFour' is compared to the commercial variety 'Driscoll Atlantis' (U.S. Plant Pat. No. 16,475), 'DrisStrawTwentyFour' has medium glossy leaves, a slightly oblique terminal leaflet base, and thin stolons that have strong anthocyanin coloration and sparse pubescence, while 'Driscoll Atlantis' has weakly glossy leaves, a rounded terminal leaflet base, and medium thick stolons that have weak to medium anthocyanin coloration and medium pubescence. Additionally, 'DrisStrawTwentyFour' has inflorescence positioned beneath the foliage, and fruit with a broad band without achenes and a coarse texture, while 'Driscoll Atlantis' has inflorescence positioned level to above the foliage, and fruit with a very narrow band without achenes and a medium texture when tasted.

We claim:

1. A new and distinct variety of strawberry plant named 'DrisStrawTwentyFour' as described and shown herein.

* * * * *